United States Patent [19]

Renauld

[11] Patent Number: 4,814,471

[45] Date of Patent: Mar. 21, 1989

[54] PROCESS FOR PREPARING SULPHONATED ORGANOSILICON COMPOUNDS

[75] Inventor: Franck A. D. Renauld, Barry, Wales

[73] Assignee: Dow Corning, Ltd., Barry, Wales

[21] Appl. No.: 163,663

[22] Filed: Mar. 3, 1988

[30] Foreign Application Priority Data

Mar. 14, 1987 [GB] United Kingdom ............... 8706092

[51] Int. Cl.$^4$ .............................. C07F 7/8; C07F 7/18
[52] U.S. Cl. .................................................... 556/428
[58] Field of Search ........................................ 556/428

[56] References Cited

U.S. PATENT DOCUMENTS

| | | | |
|---|---|---|---|
| 2,997,457 | 8/1961 | Kantor | 556/428 X |
| 3,187,033 | 6/1965 | Nitzsche et al. | 260/448.2 |
| 3,328,449 | 6/1967 | Haluska | 260/448.2 |
| 3,465,015 | 9/1969 | Speier | 260/448.2 |
| 3,507,897 | 4/1970 | Kanner | 260/448.2 |
| 3,531,507 | 9/1970 | Morehouse | 556/428 |
| 3,660,452 | 5/1972 | Morehouse | 260/448.2 |
| 4,082,790 | 4/1978 | Speier | 260/448.8 |
| 4,235,638 | 11/1980 | Beck et al. | 556/428 X |
| 4,777,277 | 10/1988 | Colas et al. | 556/428 X |

Primary Examiner—Paul F. Shaver
Attorney, Agent, or Firm—Marc C. Pawl

[57] ABSTRACT

Organosilanes and organosiloxanes characterized by the group $\equiv SiQSO_3^- Na^{30}$ in which Q is alkylene or phenylene are prepared by reacting the corresponding mercaptopropylsubstituted silanes and siloxanes with sodium permanganate.

The products have surface active properties and are useful as emulsifying agents and for reducing the surface tension of aqueous media.

5 Claims, No Drawings

PROCESS FOR PREPARING SULPHONATED ORGANOSILICON COMPOUNDS

This invention relates to a process for the preparaton of organosilicon compounds having in the molecule at least one sulphonated hydrocarbon group attached to silicon.

Organosilanes and organosiloxanes having silicon-bonded groups containing a sulphonate group are known. Various methods for the preparation of such silanes and siloxanes have been described in the patent and other technical literature. For example, British Pat. Nos. 1 270 977 and 1 198 096 describe the preparation of sulphonate-containing organosilicon compounds by the reaction of the corresponding epoxylated silane or siloxane with a primary or secondary amine sulphonate, e.g. sodium methyl taurine, or with sodium bisulphite respectively. British Pat. No. 1 030 888 discloses the reaction of a mercaptoethyl silicon compound with sodium methoxide and further reaction of the product with a hydroxypropane sulphonic acid and British Pat. No. 1 005 872 is concerned with the manufacture of sulphonated organosilicon products involving reacting the corresponding unsaturated organosilicon compound with an alkali metal bisulphite or pyrosulphite.

The known processes, however, have certain disadvantages. Thus, one or more of the reactants may be expensive or not readily available. In the case of British Pat. No. 1 005 872 the process has to be performed at high pressures.

According to the present invention there is provided a process for the preparation of sulphonated organosilicon compounds which comprises reacting (1) an organosilicon compound which is (a) a silane represented by the general formula R$_3$SiQSH or (b) an organosiloxane having at least one unit represented by the general formula

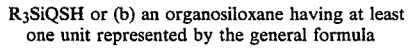

any other units present in the organosiloxane being those represented by the general formula

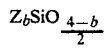

wherein each R and each R' represents a methyl, ethyl or phenyl group or the group —OX in which X is methyl, ethyl or methoxyethyl, Q represents an alkylene group having from 2 to 10 carbon atoms or a phenylene group, Z represents a hydrogen atom or a monovalent hydrocarbon group having from 1 to 18 carbon atoms, a has a value of 0, 1 or 2 and b has a value of 0, 1, 2 or 3, with (2) sodium permanganate.

The organosilicon compounds prepared according to the process of this invention are characterised by the presence of the group ≡SiQSO$_3$⁻Na⁺, there being one such group in the silane product and one or more such groups in the siloxane products. The silane products may thus be represented by the general formula R$_3$SiQSO$_3$⁻Na⁺ and the siloxane products may be homopolymers of units represented by the general formula

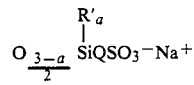

or copolymers of one or more such units with units represented by the general formula

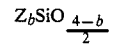

wherein R, R', Q, Z, a and b have the meanings hereinbefore ascribed.

In the unit general formulae of the reactants and products herein each R and each R' may represent a methyl, ethyl or phenyl group but are preferably each methyl. The group Q may be an alkylene group having from 2 to 10 carbon atoms, for example —CH$_2$CH$_2$—, —(CH$_2$)$_4$— and —CH$_2$CH$_2$C(CH$_3$)$_2$— or it may be phenylene. From the standpoint of commercial availability Q is preferably the group —(CH$_2$)$_3$— or the group —CH$_2$CH.CH$_3$CH$_2$—. The substituent Z may be a hydrogen atom or any monovalent hydrocarbon group having from 1 to 18 carbon atoms. Examples of Z groups therefore are alkyl groups e.g. methyl, ethyl, propyl, trimethylpentyl, dodecyl and tetradecyl, alkenyl groups e.g. vinyl and allyl, aryl, alkaryl and aralkyl groups e.g. phenyl, 2-phenylpropyl and tolyl. When the intended application of the organosilicon product is related to its surface active properties it is preferred that at least 65% of the total R, R' and Z groups in the molecule are methyl groups.

The mercaptoalkyl silanes and siloxanes (1) which are employed in the process of this invention are known materials. They may be prepared, for example, by the reaction of hydrogen sulphide on the corresponding chloroalkyl-substituted organosilicon compound as described in British Pat. No. 1 512 734. Organosilicon compounds (1) wherein Q represents an arylene, aralkylene or alkarylene group may be prepared by the method disclosed in British Pat. No. 1 217 848.

The reaction between the organosilicon compound (1) and the sodium permanganate may be performed in any convenient manner. For example, the sodium permanganate may be added directly to the organosilicon compound and the reaction allowed to proceed. A more efficient method of carrying out the reaction, however, comprises forming a dispersion of the organosilicon compound in water and thereafter adding the sodium permanganate as an aqueous solution. Reaction between (1) and (2) can occur at normal room temperature or lower and is preferably carried out at temperatures between 1° C. and 30° C. Temperatures above 30° C. may lead to the scission of siloxane bonds and are normally undesirable when the organosilicon compound (1) is a siloxane. The reaction is highly exothermic and it is thus preferred to cool the reaction mixture prior to and/or during the addition of the sodium permanganate.

The relative proportions of the reactants employed in the process of the invention will depend on the number of —SH groups present in (1). The reaction proceeds on the basis of 2 moles of sodium permanganate per —SH group and generally it is preferred to employ such a ratio or a slight excess of sodium permanganate. When the reaction has proceeded to the desired degree the excess sodium permanganate may be removed from the reaction mixture by the addition of an alcohol, preferably methyl alcohol. Such addition forms an aldehyde which may be removed by distillation. The manganese dioxide which is formed during the preparative and recovery reactions can be removed by filtration. Any trace amounts of sodium hydroxide which may be present can, if desired, be neutralised by the addition of an acid.

The sulphonated organosilicon compounds obtained by the process of this invention may vary from mobile liquids to solids depending on the proportion of sulphonate groups present. If the proportion of such groups is sufficiently high the products are water-soluble. The compounds possess both hydrophilic and hydrophobic groups in the same molecule and exhibit significant surface active properties. They are thus useful as emulsifying agents and for reducing the surface tension of aqueous media.

The following examples, in which Me represents the methyl group illustrate the invention.

EXAMPLE 1

Mercaptopropylheptamethyltrisiloxane (17.76 g, 0.06 mole) was dispersed in water (20 g) with rapid stirring and the suspension cooled to 5° C. To the suspension was then slowly added a solution of sodium permanganate (19.17 g, 0.12 mole) in water (150 g), the temperature being maintained at 5° C. throughout the addition step. When all of the permanganate solution had been added the reaction mixture was allowed to warm to room temperature and stirred for 30 minutes. Methyl alcohol (100 g) was then added to remove the excess sodium permanganate and the manganese dioxide resulting from the addition removed by filtration. After removal of volatile materials at 80° C. and 10 mmHg the product remaining (19.9 g: 90.4% yield) was

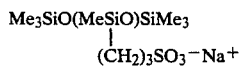

Me$_3$SiO(MeSiO)SiMe$_3$
|
(CH$_2$)$_3$SO$_3^-$Na$^+$

It was a white, hygroscopic solid and analysis yielded the following data
Na$^+$—5.79% (theory: 6.28%)
S—7.66% (theory: 8.74%)
IR—1220 cm$^{-1}$ (SO$_3$—Na$^+$) 1260, 850-800 cm$^{-1}$ (SiCH$_3$) 1110-1000 cm$^{-1}$ (Si—O—Si)
When 1 g of this solid was dissolved in 100 ml of water the resulting solution had a surface tension of 21 dyne cm$^{-1}$.

EXAMPLE 2

The siloxane (26.22 g, 0.03 mole)

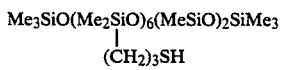

Me$_3$SiO(Me$_2$SiO)$_6$(MeSiO)$_2$SiMe$_3$
|
(CH$_2$)$_3$SH was dispersed in water (40 g) and the dispersion cooled to 5° C. To the stirred dispersion was added slowly a solution of sodium permanganate (19.17 g, 0.12 mole) in water (100 g), the temperature being maintained at approximately 5° C. throughout the addition. When addition of the solution had been completed the reaction mixture was stirred for 30 minutes at room temperature and the product recovered employing methyl alcohol (50 g) as described in Example 1.

The product (24.3 g: 80% yield), a white solid, was

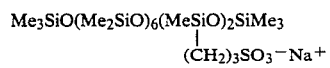

Me$_3$SiO(Me$_2$SiO)$_6$(MeSiO)$_2$SiMe$_3$
|
(CH$_2$)$_3$SO$_3^-$Na$^+$

Analysis of the product gave the following data
Na$^+$—3.96% (theory: 4.53%)
S—5.99% (theory: 6.31%)
IR—1220 cm$^{-1}$ (SO$_3^-$Na$^+$); 1260, 850-800 cm$^{-1}$ (SiCH$_3$) 1110-1000 cm$^{-1}$ (Si—O—Si)
A solution of 1 g of this solid in 100 ml of water had a surface tension of 32 dyne cm$^{-1}$.

When the processes of Examples 1 and 2 were repeated employing potassium permanganate in place of the sodium permanganate the yields of the sulphonated siloxanes varied from 0 to 24%.

EXAMPLE 3

Employing the procedure of Example 1 the siloxane

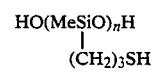

HO(MeSiO)$_n$H
|
(CH$_2$)$_3$SH in which n=approximately 4 to 40, was reacted with sodium permanganate to give as the product

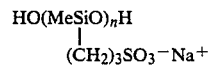

HO(MeSiO)$_n$H
|
(CH$_2$)$_3$SO$_3^-$Na$^+$

That which is claimed is:
1. A process for the preparation of sulphonated organosilicon compounds which comprises reacting (1) an organosilicon compound which is (a) a silane represented by the general formula R$_3$SiQSH or (b) an organosiloxane having at least one unit represented by the general formula

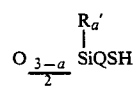

$$O_{\frac{3-a}{2}}\text{SiQSH}$$ with R$_a'$ substituent any other units present in the organosiloxane being those represented by the general formula

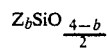

$$Z_b\text{SiO}_{\frac{4-b}{2}}$$

wherein each R and each R' represents a methyl, ethyl or phenyl group, or the group —OX in which X is methyl, ethyl or methoxyethyl, Q represents an alkylene group having from 2 to 10 carbon atoms or a phenylene group, Z represents a hydrogen atom or a monovalent hydrocarbon group having from 1 to 18 carbon atoms, a has a value of 0, 1 or 2 and b has a value of 0, 1, 2 or 3, with (2) sodium permanganate.

2. A process as claimed in claim 1 wherein at least 65 percent of the total R, R' and Z groups are methyl groups.

3. A process as claimed in claim 1 wherein the reaction is carried out in an aqueous medium.

4. A process as claimed in claim 3 wherein the reaction is carried out at a temperature below 30° C.

5. A process as claimed in claim 3 which comprises the further step of contacting the reaction mixture with an aliphatic alcohol to remove any excess sodium permanganate remaining therein.

* * * * *